United States Patent
Kim et al.

(10) Patent No.: US 8,552,253 B2
(45) Date of Patent: Oct. 8, 2013

(54) SCREENING OF DRUG FOR ATTENTION DEFICIT HYPERACTIVE DISORDER BY USING GIT1 KNOCK-OUT MICE AS A NOVEL ADHD MOUSE MODEL

(75) Inventors: Eunjoon Kim, Daejeon (KR); Changwon Kang, Daejeon (KR); Won Mah, Daejeon (KR); Hyejung Won, Daejeon (KR); Eun-Kyoung Hahm, Daejeon (KR); Eunjin Kim, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 13/446,789

(22) Filed: Apr. 13, 2012

(65) Prior Publication Data

US 2013/0061338 A1    Mar. 7, 2013

(30) Foreign Application Priority Data

Sep. 2, 2011  (KR) ........................ 10-2011-0089182

(51) Int. Cl.
*G01N 33/00* (2006.01)
*A01K 67/027* (2006.01)

(52) U.S. Cl.
USPC ..................................... 800/3; 800/18; 800/9

(58) Field of Classification Search
USPC ................................................... 800/3, 18, 9
See application file for complete search history.

(56) References Cited

FOREIGN PATENT DOCUMENTS

| KR | 10-0827470 | 4/2008 |
|---|---|---|
| WO | 03/088967 | 10/2003 |

OTHER PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Russell et al., (2005) Behavioral and Brain Functions, vol. 1(9), 1-17.*
Won et al. (May, 2011) Nat. Med., vol. 17 (5), 566-573.*
Lee et al. (May, 2011) Nat. Med., vol. 17(5), 541-542.*
Hyejung Won, et al., "GIT1 is associated with ADHD in humans and ADHD-like behaviors in mice," Nature Medicine, May 2011, pp. 566-573, vol. 17, No. 5.
Cynthia L. Leibson, et al., "Use and Costs of Medical Care for Children and Adolescents With and Without Attention-Deficit/Hyperactivity Disorder," JAMA, Jan. 3, 2001, pp. 60-66, vol. 285, No. 1, American Medical Association.
Boaz Wultz, et al., "The Spontaneously Hypertensive Rat as an Animal Model of Attention-Deficit Hyperactivity Disorder: Effects of Methylphenidate on Exploratory Behavior," Behavioral and Neural Biology, 1990, pp. 88-102, vol. 53.
Vivienne Russell, et al., "Differences between electrically-, ritalin- and D-amphetamine-stimulated release of [3H] dopamine from brain slices suggest impaired vesicular storage of dopamine in an animal model of Attention-Deficit Hyperactivity Disorder," Behavioural Brain Research, 1998, pp. 163-171, vol. 94.
Raul R. Gainetdinov, et al., "Role of Serotonin in the Paradoxical Calming Effect of Psychostimulants on Hyperactivity," Science, Jan. 15, 1999, pp. 397-401, vol. 283.
E. J. Hess, et al., "Spontaneous Locomotor Hyperactivity in a Mouse Mutant with a Deletion Including the Snap Gene on Chromosome 2," The Journal of Neuroscience, Jul. 1992, pp. 2865-2874, vol. 12, No. 7.
James M. Swanson, et al., "Etiologic Subtypes of Attention-Deficit/Hyperactivity Disorder: Brain Imaging, Molecular Genetic and Environmental Factors and the Dopamine Hypothesis," Neuropsychol Rev, 2007, pp. 39-59, vol. 17.
Bryan Kolb, et al., "Amphetamine or cocaine limits the ability of later experience to promote structural plasticity in the neocortex and nucleus accumbens," PNAS, Sep. 2, 2003, pp. 10523-10528, vol. 100, No. 18.

* cited by examiner

*Primary Examiner* — Anne Marie S Wehbe
(74) *Attorney, Agent, or Firm* — Cantor Colburn LLP

(57) ABSTRACT

Provided is a method of using any mammal except humans, in particular, a mammal as an attention deficit hyperactivity disorder model, wherein genes of G protein-coupled receptor kinase interacting protein 1 (GIT1) as a neuronal synapse protein in the brain are knocked out from the mammal. In addition, disclosed is analysis of GIT1 knock-out mice in aspects of molecular biology, cellular biology, electrical biology and animal behavior and, more particularly, a screening method of novel drug, wherein excessive behavior as an attention deficit hyperactive disorder as well as recovery of theta wave in the frontal lobe are observed by administering a candidate material of the drug, thereby inducing recovery of the attention deficit hyperactivity disorder.

3 Claims, 8 Drawing Sheets

SCREENING OF DRUG FOR ATTENTION DEFICIT HYPERACTIVE DISORDER BY USING GIT1 KNOCK-OUT MICE AS A NOVEL ADHD MOUSE MODEL

CROSS-REFERENCE TO RELATED APPLICATIONS

This application claims priority under 35 U.S.C. §119 to Korean Patent Application No. 10-2011-0089182, filed on Sep. 2, 2011, in the Korean Intellectual Property Office, the disclosure of which is incorporated herein by reference in its entirety.

TECHNICAL FIELD

The following disclosure relates to use of animals except for humans, especially, a mammal wherein genes of a neuronal synapse protein, that is, G protein-coupled receptor kinase interacting protein 1 are deleted ('GIT1 knock-out') in the brain of the mammal, as an attention deficit hyperactivity disorder model.

Also, the present invention relates to analysis of GIT1 knock-out mice in aspects of molecular biology, cellular biology, electrical biology and animal behavior and, in particular, provides a novel drug screening method for inducing recovery of attention deficit hyperactivity disorder by observing excessive behavior as a symptom of the attention deficit hyperactivity disorder through administration of a drug comprising a candidate material, as well as recovery of theta brain waves in the front lobe.

BACKGROUND

Attention deficit hyperactivity disorder (hereinafter, referred to as 'ADHD') is a widely known mental disease showing attention deficit, hyperactivity, impulsivity, etc. This disease has high prevalence in about 5% of school children all over the world, whom have ADHD related symptoms. According to the study of Leibson, et al. (2001, JAMA, 285, 60-66.), a household with a child having ADHD symptom spends about twice as much or more on healthcare than that of the other households without ADHD children. In addition, parents of ADHD children generally suffer from stress, excruciation and, even hypochondriac symptoms, etc.; therefore, a need for ADHD treatment is being highlighted throughout the society. Owing to such high prevalence and influence thereof upon the society, global researches on identification of a pathological mechanism for ADHD have been conducted.

More particularly, in order to stipulate the ADHD mechanism, a number of hypotheses have been proposed and, among these, a dopamine hypothesis is receiving the most attention. However, genome-wide linkage or association studies demonstrated that various genes unrelated to dopamine are associated with ADHD. In addition, specific properties and high geneticity of ADHD strongly suggest existence of various ADHD-related genes.

Meanwhile, the histamine H3 receptor antagonist has functional effects in relation to a wide range of diseases including ADHD, obesity, epilepsy, psychosis, hypochondria, pain, drug abuse/toxicity, and so forth. Furthermore a number of novel compounds are being produced for the treatment of ADHD, cognitive disorders (e.g., Alzheimer's disease), sleep disorders and/or psychosis.

In addition to development of numerous compounds, a variety of ADHD animal models for ADHD studies have been proposed. For instance, Wultz, et al. (Behavioral and Neural Biology, 1990, 53(1), 88-102.) disclosed that existing spontaneous hypertensive rat (hereinafter, referred to 'SHR') may be utilized as an ADHD model animal and are now practically used in some ADHD-related studies. In particular, a problem in secretion and metabolism of dopamine in SHR has been found (Russell, et al., Behav. Brain. Res., 1998, 163-171.), which was a significant result in order to demonstrate an important role of dopamine in ADHD. However, noticeable study results demonstrating pathogenic causes of ADHD-associated symptoms of SHR were not reported. Although correlation of dopamine with ADHD is continuously found, a relationship therebetween has yet to be clearly demonstrated. Gainetdinov, et al. (Science, 1999, 283(5400), 397-401.) has proposed a novel ADHD model animal through experimentation using mice with gene deletion of a dopamine transporter (DAT-KO mice). The above article directly demonstrates that a protein relating to the uptake of dopamine is related to ADHD, which is a new discovery to support existing dopamine hypothesis. However, DAT-KO mice also show study results conflicting with the dopamine hypothesis, for example, importance of serotonin rather than dopamine in recovery of ADHD symptoms.

Hess, et al. (J Neurosci., 1992, 12(7), 2865-74.) have taken notice of hyperactivity in mutant mice having partially deleted chromosome 2, Coloboma (hereinafter, referred to as 'Coloboma'). Afterward, it was found from gene linkage studies that a protein named SNAP-25 present in the deleted chromosome 2 is associated with ADHD. However, further studies on ADHD mechanism of Coloboma mice are now at a standstill since research of the basic origin of ADHD has not been attempted.

Other than the ADHD model animal described above, various models have been proposed. However, they did not show ADHD relating genes or were limited to studies in an animal behavior experimentation level. Therefore, demands for approaches in aspects of molecular biology, cellular biology and/or electric physiology have become conspicuous in order to identify basic origins of ADHD. ADHD study results obtained through such approaches may impart a broader view of the basic origins of ADHD and, in addition, make it possible to discover and/or propose novel medicines. Among existing ADHD medicines, amphetamine and methylphenidate classified as a nerve stimulator are known. According to reports by Swanson, et al. (Neuropsychol. Rev., 2007, 17, 39-59.), precaution of the nerve stimulator to treat ADHD is continuously increased since 1990.

However, such nerve stimulator may derive significant side effects such as hallucination and anxiety. The report by Fleckenstein, et al. (Annu. Rev. Pharmacol. Toxicol., 2007, 47, 681-698.) suggested that a nerve stimulator may damage dopamine secreting nerve cells and/or serotonin secreting nerve cells; Kolb et al. (Proc. Natl. Acad. Sci. USA, 2003, 100, 10523-10528.) disclosed a research result wherein continuous dose of amphetamine may influence structural plasticity of nerve cells, in turn restricting learning and memory performance through new experiences. Such side effects, neuro-cellular toxicity and adverse influence of the nerve stimulator upon memory and learning performance may raise a requirement for novel ADHD medicines.

G protein-coupled receptor kinase interacting protein 1 (hereinafter, referred to as 'GIT1') is a multi-functional adaptor protein and comprises several domains including, for example, GTPase-activating domain for ARF small GTPases (ARF GAP domain). The ARF GAP domain of GIT1 has an important role in transporting beta 2-adrenaline receptor and other G-protein combined receptor through phagocytosis. In addition, GIT1 combines with a variety of signal transfer proteins such as GRK, PIX, FAK, PLCγ, MEK1, Piccolo, liprin-α, paxillin, etc., as well as adaptor proteins, thus meaning that GIT1 can function as a signal transfer adaptor.

GIT1 in the brain is substantially present in synapse, and participates in growth of axons, formation of dendritic spine-structure, synapse formation, localization of synapse AMPA [2-amino-3-(5-methyl-3-oxo-1,2-oxazol-4-yl)propanoic acid] receptor (referred to as 'AMPA receptor localization'), and so forth. GIT1 combines with a Huntington protein associated with Huntington's disease and a research result of observing a division of GIT1 protein in the brain of a patient suffering from Huntington's disease has been reported. Further, another research result obtained using GIT1 knock-out mice demonstrated growth of dendrites, decrease in density of dendritic spines, and deterioration in learning and memory performance (Prashanthi Menon, et al., Brain Res. 2010; 1317: 218226), thereby suggesting that GIT1 is in a charge of significant functions in the brain.

However, current GIT1 studies are limited to molecular biological and cellular biological applications, and behavior experimentations in the related art have substantially not proposed a correct mechanism sufficiently explaining and/or supporting results of the experimentations.

The present inventors have executed experimentations such as electroencephalogram (hereinafter, referred to as 'EEG') measurement in a system level, using GIT1 knock-out mice as an ADHD model animal, in addition to existing methods based on molecular biology, cellular biology and animal behavior research, in order to provide genetic causes of basic origins for ADHD. Further, there is also provided a screening method of a novel ADHD medicine using GIT1 knock-out mice showing ADHD symptoms.

PREVIOUS ART DOCUMENT

Patent Document (Patent Document 1) KR Registration number 10-0827470: (1-4-Piperidinyl)benzimidazole derivatives useful as histamine H3 antagonists, Registration Date: 2008 Apr. 28, Grantee: SCHERING CORPORATION.

Non-patent Document (Non-patent Document 1) Leibson, et al., JAMA, 2001, 285, 60-66.
(Non-patent Document 2) Wultz, et al., Behavioral and neural biology, 1990, 53(1), 88-102.
(Non-patent Document 3) Russell, et al., Behav. Brain. Res. 1998, 163-171.
(Non-patent Document 4) Gainetdinov, et al., Science, 1999, 283(5400), 397-401.
(Non-patent Document 5) Hess, et al., J Neurosci. 1992, 12(7), 2865-74.
(Non-patent Document 6) Swanson, et al., Neuropsychol. Rev. 2007, 17, 39-59.
(Non-patent Document 7) Kolb, et al., Proc. Natl. Acad. Sci. USA, 2003, 100, 10523-10528.

SUMMARY

An object of the present invention is to provide animals except humans, in particular, mammals wherein genes of a neuronal synapse protein in the brain, that is, G protein-coupled receptor kinase interacting protein 1 (GIT1) are knocked out from the mammals, as an animal model for attention deficit hyperactivity disorder (ADHD).

Another object of the present invention is to provide a screening method of a novel drug that includes using a GIT1 knock-out mouse and administering an ADHD candidate material of the drug to the mouse, thus inducing recovery of the disease.

According to the present invention, there is provided a method of using a GIT1 knock-out mammal except humans, capable of screening a drug for protection or treatment of diseases in the central nervous system or mental diseases from mammals including humans, suffering from attention deficit hyperactivity disorder as a brain disease, while enabling protection and/or treatment of such diseases. The central nervous systemic diseases and mental diseases may include, for example, any one selected from a group consisting of sleep disorder, awakening disorder, narcolepsy, cognitive disorder, ADHD, obesity, epilepsy, schizophrenia, hypochondria, pain and drug abuse/toxicity.

Candidate materials for protection or treatment of attention deficit hyperactivity disorder (ADHD) may include at least one selected from methylphenidate, d-Amphetamine and Pemoline, which are cognitive enhancers. However, these are antipsychotic drugs having a mechanism to stimulate the central nervous system and may cause various adverse effects, in particular, amnesia, rebound phenomena, decrease of appetite, displeasure, dizziness, stimulation sensitivity, anxiety and impatientness, and so forth.

Other than the foregoing, the candidate materials may also include, for example; peptide, protein, non-peptide compounds, synthetic compounds, fermented products, cell extract, plant extract, animal tissue extract, plasma, or the like, and these may be a novel compound or a compound well known in the art. The foregoing candidate material may be present in a salt form. Salts of the candidate materials are based on physiologically acceptable acid (e.g., inorganic acid) or base (e.g., organic acid) and, among these, physiologically acceptable acid added salts are preferably used. Such salts may include, for example; salts of inorganic acid (e.g., hydrochloric acid, phosphoric acid, hydrobromic acid, sulfuric acid, etc.); and salts of organic acid (e.g., acetic acid, formic acid, propionic acid, fumaric acid, maleic acid, succinic acid, tartaric acid, citric acid, malic acid, oxalic acid, benzoic acid, methane sulfonic acid or benzene sulfonic acid.

A method for administration of the candidate material may include, for example, suitably selected from oral, intravenous, subcutaneous, intracutaneous or peritoneal administration, in consideration of symptoms of subject animals, features of candidate materials, etc. Moreover, a dose of administering the candidate material may be suitably selected along with administering methods, features of candidate materials, etc.

An animal used herein for administration of the candidate material may be at least one of mammals, preferably, selected from mouse, rat, pig and ape. More preferably, a GIT1 knock-out mouse invented by the present inventors is used.

The GIT1 gene is present in a synapse of the brain and known to participate in growth of axons, formation of dendritic spine structure, synapse formation, synapse AMPA receptor localization, etc. Also, GIT1 combines with Huntington protein, in which the GIT1 protein is observed to be divided in the brain of a patient suffering from Huntington's disease. In addition, according to other research results obtained using GIT1 knock-out mice, it can be confirmed that GIT1 has important functions in the brain, in particular, growth of dendrites, decrease in density of dendritic spines, and deterioration in learning and memory performance.

A screening method of medical drugs or mental diseases according to the present invention may use nerve cells, cells including specific genes concentrated therein and an animal model and, more particularly, include at least one selected therefrom, without being particularly limited thereto.

Examples of the nerve cells may include dopamine nerve cells such as MES23.5 cell, MN9D cell, PC12 cell, SHSY5Y cell, CATH.a cell, etc., and the dopamine nerve cell is used in search of a bio-marker and a nerve protecting target changed in the dopamine nerve cell. More particularly, in order to find medicines and bio-markers desired for nerve protection using changes exhibited when DJ-1, Parkin and/or PINK1 genes as mutagens with familial Parkinson's disease having lost functions, numerous studies are currently being attempted. However, the above cell models do not maintain an intracellular environment formed of dopamine nerve cells alone but have disadvantages such as different cell origins and co-existence of genetic features of fused cells.

In the screening method using a cell model, which has specific genes accumulated therein, the cell model with partial loss of gene such as siRNA, instead of overall gene loss, and is insufficient to seek for targets to respond changes exhibited during loss of perfect gene functions. In addition to the foregoing cell model, an animal model used for screening a medicine and drug for mental diseases according to the present invention may include at least one selected from, for example, SHR, mouse having gene deletion of a dopamine transmitter (DAT-KO mice), Parkinson DJ-1 knock-out animal, a Coloboma mouse without SNAP-25 protein and a GIT1 knock-out mouse.

However, the above animal model is known to entail problems in that it is difficult to obtain a sufficient amount of pure dopamine cells to execute molecular and/or biochemical studies and to extract a practical sample from Parkinson's disease patients. For instance, a concrete mechanism of a pathogenic gene of Parkinson's disease, DJ-1, has not yet been disclosed and a fact that Parkinson's disease is derived where a protein does not normally generate due to mutation of DJ-1 gene, is still uncertain.

Accordingly, it can be seen that the present invention preferably uses GIT1 knock-out mice for screening a medicine or drug through different experimentations including, for example, attention deficit, hyperactivity, diffuseness and/or behavior disorder tests.

A screening method using GIT1 knock-out mice according to the present invention may include, in particular, at least one selected from open field test, home-cage activity test, Morris water maze test, novel object recognition test and electroencephalogram ('EEG') test.

In the open field test and home-cage activity test described above, candidate materials are administered to GIT1 knock-out mice may show effects of improving hyperactivity, compared to normal mice as a control. For the Morris water maze test and the novel object recognition test, memory, space sensing ability and learning performance are enhanced by the screening method. Therefore, it can be seen that the foregoing mice are used as a good animal model for selection of candidate materials. In particular, it is understood that GIT1 knock-out mice may be used for analysis of a waveform in an abnormal theta wave section and a power spectrum density in the frontal lobe by a screening method using EEG in a systemic level, thereby being used as a standard for assessment of the cerebrum performance in a mammal having ADHD and as a subject used for a novel assessment method of basic origins thereof.

Other features and aspects will be apparent from the following detailed description, the drawings, and the claims.

DETAILED DESCRIPTION OF EMBODIMENTS

Hereinafter, the present invention will be described in more detail by preferred exemplary embodiments thereof, without being particularly limited to such embodiments. It will be apparent to those skilled in the related art that various alterations and modifications within the idea and scope of the present invention may be possible.

In this regard, technical and/or scientific terminologies used in the detailed description herein have meanings generally understood by those skilled in the related art, to which the present invention pertains, unless otherwise stated.

Additionally, in the following description and the accompanying drawings, a detailed description of technical configurations and/or functions well known in the art will be omitted for brevity.

Example 1

Identification of GIT1 Knock-Out Mice

An embryo stem cell used herein for fabrication of GIT1 knock-out mice (ES cell, FHCRC-GT-S10-12C1) was purchased from Fred Hutchinson Cancer Center. ES cell (embryonic stem cell) was incubated in a culture medium including β-mercaptoethanol at 500λ, 1% (v/v) penicillin/streptomycin and 15% (v/v) FBS (fetal bovine serum)(Dulbecco's Modified Eagle Medium, DMEM, Gibco) and then, the treated cell was microinjected into blastcyst of C57BL/6 mice. The injected blastcyst was implanted to a uterus of an ICR surrogate mother mouse to fabricate a chimera mouse. Genotype of the chimera mouse was confirmed through expression of aguti hair and a polymerase chain reaction (PCR). The chimera mouse was subjected to propagation by interbreeding C57BL/6 type and 129/SV/Jae type mice. Using a mouse created by hybridization of heterozygote mice obtained from respective types, the present experimentation was executed.

Example 1-1

Confirmation of GIT1 Knock-Out Using PCR

In order to identify GIT1 knock-out in Example 1, two different experimental methods were used. The first one is a PCR using a primer set to amplify a specific part of GIT1 gene, thus confirming whether there is GIT1 knock-out or not. Additionally, using a primer capable of amplifying βgeo as an external gene contained only in a GIT1 knock-out mouse and a hetero-mouse, the genotype of each mouse was correctly identified. Base sequences of the primer set used in the PCR are shown in Table 1.

TABLE 1

Primer sets for confirmation of genotype

| Name | Length (-mer) | Sequences (5' to 3') |
|---|---|---|
| GIT1+ | 22 | GGA ACT CTG ATG GTG ACG TTG G |
| GIT1- | 22 | AAT GCA GAG CCA GAC ACC TCA C |
| βgeo+ | 24 | TTA TCG ATG AGC GTG GTG GTT ATG |
| βgeo- | 25 | GCG CGT ACA TCG GGC AAA TAA TAT C |

Figure 1:
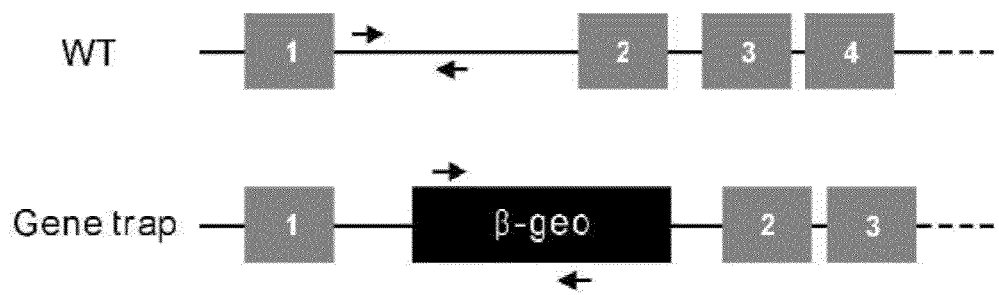
FIG. 1 illustrates a condition of GIT1 gene having gene-trap inserted in intron 1 thereof (the number of axons is indicated as numerals in respective grey boxes, β-geo denotes a combination of β-galactosidase and neomycin, and arrows mean a primer set used for examination of genotypes)
Figure 2A:
FIG. 2 illustrates PCR result (FIG. 2A) of examining gene types GIT1 knock-out mice used in the present invention, and a Western blot test result showing protein expression (FIG. 2B)

The location of the primer sets in Table 1 is illustrated in FIG. 1. In the case where the PCR is executed using the foregoing primer sets, DNA debris with a size of 500 base pairs was amplified in a normal mouse while DNA debris having a size of 680 base pairs was amplified in a GIT1 knock-out mouse. On the other hand, the hetero mouse showed amplification of two different base pair debris having both the sizes described above. Results observed from the PCR are shown in FIG. 2A.

A mixture used for the PCR was prepared of; 14.8 μl of doubly distilled water, 1.6 μl of 10 mM dNTP, 2.0 μl of Taq polymerase buffer, 0.4 μl of Taq polymerase (Sungenetics), 0.1 μl (100 pM) of primer, and 1 μl (100 μg/ml) of DNA prototype. Through PCR, a genotype of the mixture was confirmed. The PCR was performed by reacting the mixture at 95° C. for 5 minutes, followed by repeating 40 times a cycle composed of reactions at 95° C. for 30 seconds, 55° C. for 30 seconds and 72° C. for 40 seconds. Following this, after reacting at 72° C. for 5 minutes, the reaction product was confirmed through electrophoresis using 1% agarose gel.

Example 1-2

Confirmation of GIT1 Knock-Out Using a Western Blotting Method

As another method for confirming GIT1 knock-out in Example 1, a western blotting method was used to detect GIT1 protein defects. In order to prepare a sample for western blotting, overall brain tissues of both a normal mouse aged at 8 weeks and a GIT1 knock-out mouse were used. The extracted brain tissue was mixed with a homogenization buffer (0.32M Sucrose, 4 mM HEPES, 1 mM $MgCl_2$, 0.5 mM $CaCl_2$, 1 mM PMSF, 5 μg/ml Pepstatin A, 2 mM Benzamidin, and 2 μg/ml Leupeptin), disrupted using a homogenizer), and the homogenized brain tissue was subjected to the Bradford experiment to determine a protein concentration of the tissue. The protein was mixed with a 2×SDS buffer (100 mM TrisCl at pH6.8, 5% β-Mercaptoethanol, 4% Sodium Dodesyl Sulfate, 0.2% BromoPhenyl Blue, and 20% glycerol) and subjected to denaturalization for 10 minutes at 100° C., thus preparing a brain tissue sample.

The brain tissue sample prepared according to the above procedure was placed on 7.5% acrylamide gel and treated through electrophoresis at 16 mA until the protein is separated. After electrophoresis, the acrylamide gel was closely attached to a nitrocellulose transfer membrane (Whatman) and completely immersed in a transfer buffer (14.4 g Glycine, 3.03 g Tris, 200 ml methanol, and 800 ml distilled water). Next, electrophoresis was conducted at 85V for 90 minutes. By the foregoing procedures, the protein moved to the transfer membrane while the moved protein was detected using GIT1 antibody.

Figure 2B:
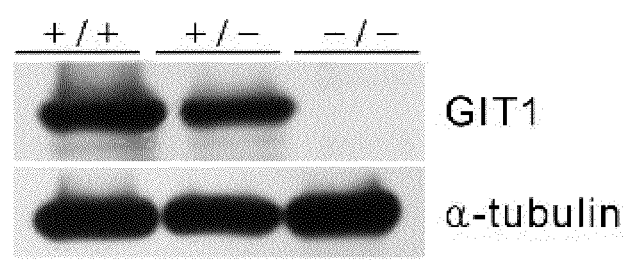

In order to execute western blotting, the transfer membrane was stained using a Ponceau S dye to detect approximate position of the protein. The membrane was washed several times using the distilled water to remove the Ponceau S dye, and maintained in a blocking solution (5% skimmed milk powder dissolved in a TBST solution) for 30 minutes. Subsequently, a reaction was performed in a TBST solution including an antibody (Neuromab) of GIT1 diluted to 1:1000 for 1 hour. In order to remove unbound antibody, which was not combined with the GIT1 protein, the reaction product was washed 3 times for 10 minutes in the TBST solution. The membrane was maintained in a TBST solution containing a secondary antibody diluted to 1:10000 for 30 minutes, to allow the secondary antibody bound to the GIT1 antibody. Then, in order to remove unbound secondary antibody, the treated product was washed three times for 10 minutes using a TBST solution. After reacting the membrane with an ECL solution (GE Healthcare), the reaction product was exposed to an X-ray film (Fujifilm) in a dark place to confirm existence of GIT1 protein. The confirmed results demonstrated that GIT1 knock-out occurs only in homotype mice having GIT1 −/−, as observed in FIG. 2B.

Example 2

Open Field Test of GIT1 Knock-Out Mouse

Figure 3A:
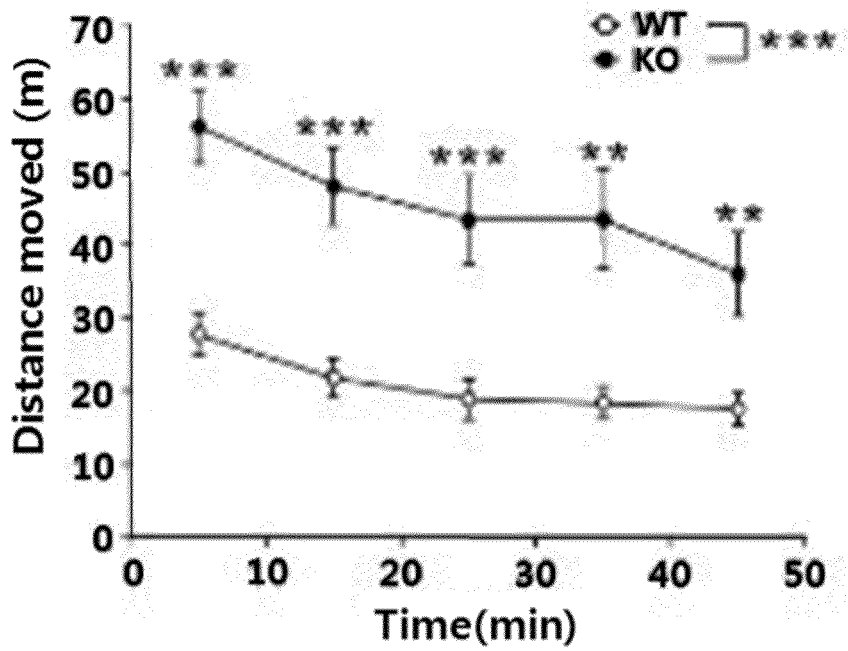
FIG. 3 illustrates hyperactivity of GIT1 knock-out mice observed in an open space (FIG. 3A) and recovery of the hyperactivity through treatment using ADHD medicines such as amphetamine and methylphenidate (FIGS. 3B and 3C)
Figure 3B:
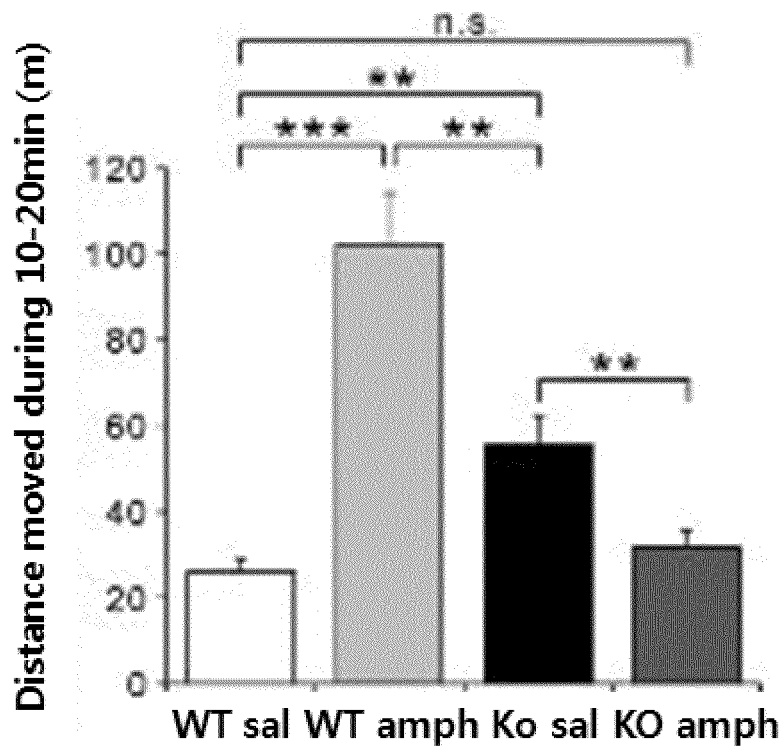
Figure 3C:
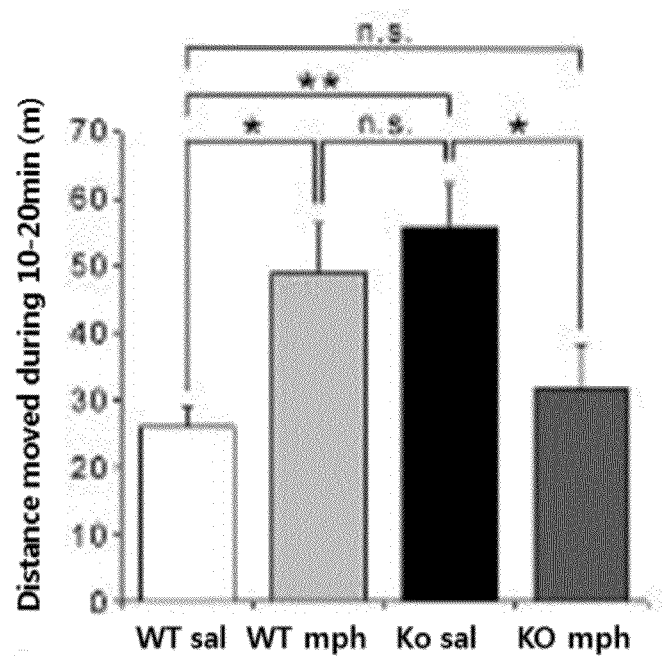

In order to observe hyperactivity of mice using the GIT1 knock-out mice of the present invention, an open field test was executed in a novel environment. A GIT1 knock-out mouse and a normal mouse (wild type) as a control, each mouse being aged 2 to 5 months, were prepared. An open space was prepared using a white box which is never exposed to the mice and has a dimension of 40-40-40 cm (width-length-height). After placing each mouse in the center of the open space and video shooting a distance of the mouse for 60 minutes, results thereof including, for example, a total distance, an average movement speed, a central space invasion rate, etc., were assayed through an activity analysis program. For analysis of behavior in the open space, amphetamine (4 mg/kg/day, one time) and methylphenidate (2 mg/kg/day, one time) used as ADHD protection drugs were administered through peritoneal injection just before placing the mouse therein, followed by immediately placing the mouse in the center of the open space. From results of the foregoing experiment, it was confirmed in FIG. 3A that the GIT1 knock-out mouse shows a longer (movement) distance, compared to the normal mouse. Also, it was observed from FIGS. 3B and 3C that administration of amphetamine and methylphenidate enables significant recovery of the movement distance of the GIT1 knock-out mouse equal to that of the normal mouse. On the other hand, a considerably long distance of the normal mouse observed in the case where the two drugs described above were administered to the normal mouse, was recognized as an analog response.

Example 3

Home-Cage Activity Test of GIT1 Knock-Out Mouse

Figure 4:
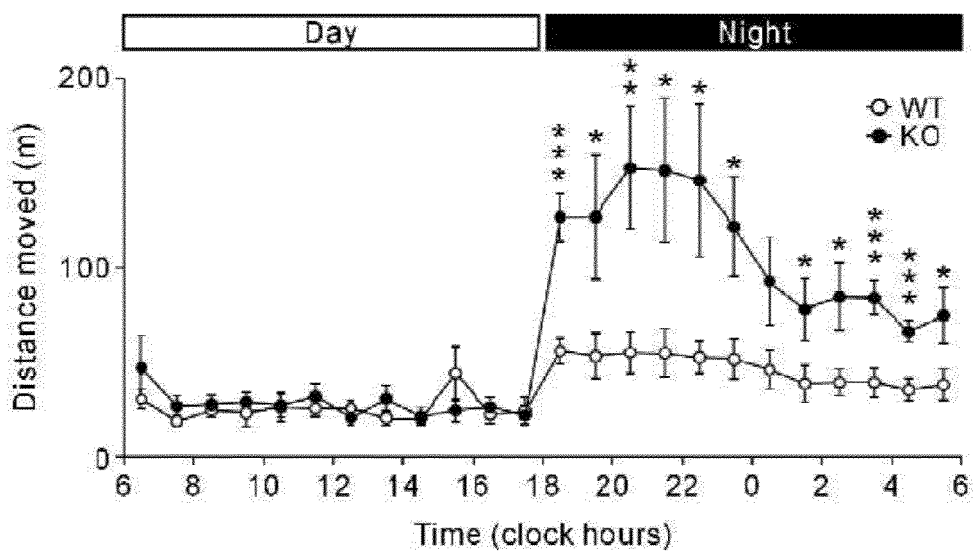
FIG. 4 illustrates results of measuring a migration distance in a familiar space of normal mice and GIT1 knock-out mice for 24 hours.

In order to observe hyperactive symptoms using the GIT1 knock-out mice of the present invention in familiar space, a home-cage activity test was executed. First, a mouse bred in a cage with a standard dimension 20×35×17 cm, was placed in an activity testing space for 24 hours to allow habituation of the mouse. Then, after video shooting behavior of the mouse during both a bright period of 12 hours and a dark period of 12 hours, a total distance was assayed through an animal activity analysis program. As a result, since the activity of the mouse is reduced during the day due to nocturnal habits thereof, the distance is very short during the day and no or little difference in distance between the normal mouse and the GIT1 knock-out mouse was observed, as shown in FIG. 4. On the contrary, at night during which the mouse is active, it was found that the GIT1 knock-out mouse of the present invention moved a longer distance in a familiar space, compared to the normal mouse and showed hyperactivity.

Example 4

Morris Water Maze Test of GIT1 Knock-Out Mouse

Figure 5A:
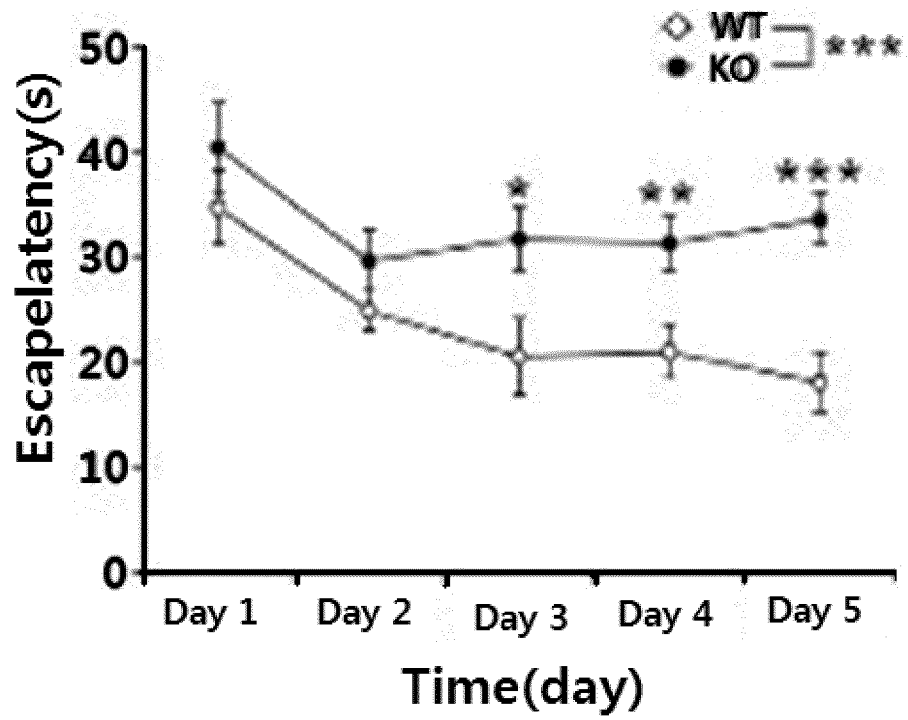
FIG. 5 illustrates results of Morris water maze test for observation of space consciousness and learning performance of GIT1 knock-out mice ('FIG. 5A' shows a decrease in time taken for normal mice and GIT1 knock-out mice to find out a footstep hidden in a training period of 5 days, 'FIG. 5B' shows the number of passing a footstep location during probe test, and 'FIG. 5C' is a holding time in respective quadrants in a water maze)
Figure 5B:
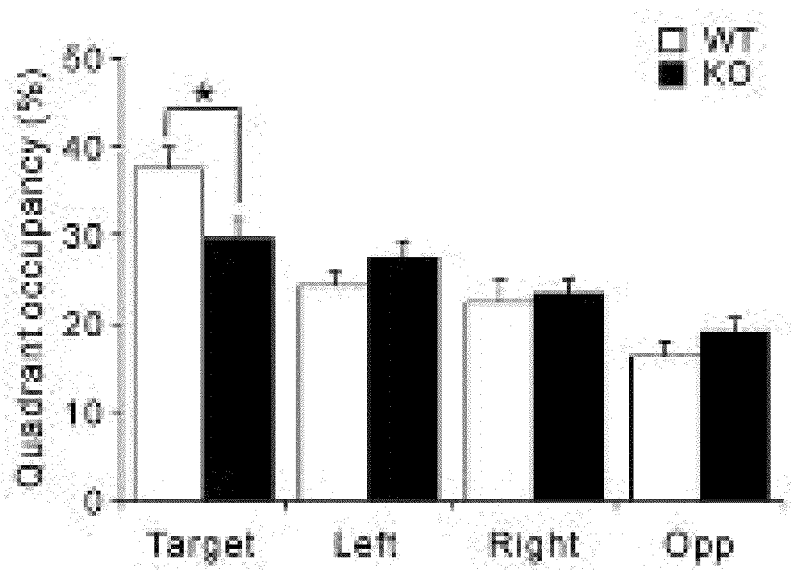
Figure 5C:
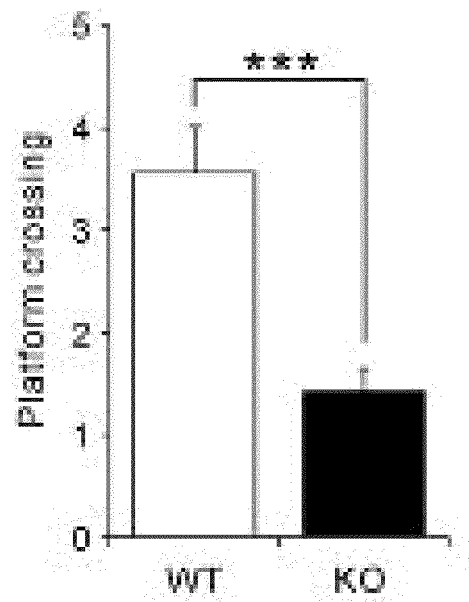

Using the GIT1 knock-out mouse of the present invention, space learning and memory performances of the mouse were determined by a Morris water maze test. A Morris water maze used herein was prepared by mounting a footstep with a diameter of 10 cm hidden in a white water bath having a diameter of 120 cm, and the mouse was subjected to training twice per day at an interval of 30 minutes, to know and memory a location of the footstep. Such training was continuously executed for 5 days. With regard to learning effects through the training, FIG. 5A demonstrated that the normal mouse found the hidden footstep earlier (within a shorter time) than the GIT1 knock-out mouse, thus confirming that the GIT1 knock-out mouse entailed problems in space recognition learning and memory performances. On the other hand, as shown in FIGS. 5B and 5C, as a result of conducting a probe test for 1 minute in the water bath having the footstep removed therefrom at Day 6 and observing a time consumption rate of the mouse in respective quadrants in the water bath, it was confirmed that the GIT1 knock-out mouse consumes less time than the normal mouse in the quadrant in which the footstep is placed. Moreover, when the number of passing a correct location of the footstep was assayed through an animal activity analysis program, it was found that the GIT1 knock-out mouse showed decreased number of correctly passing the location of the footstep, compared to the normal mouse.

Example 5

Novel Object Recognition Test of GIT1 Knock-Out Mouse

Figure 6A:
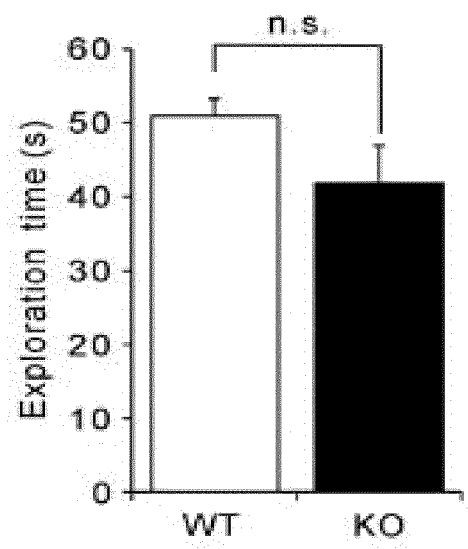
FIG. 6 illustrates results of object recognition and the object recognition test to observe learning performance ('FIG. 6A' is a total object searching time during a sample period, 'FIG. 6B' is preference for a novel object observed during a test period, and 'FIG. 6C' shows recovery of object recognition performance of GIT1 knock-out mice by amphetamine treatment)
Figure 6B:
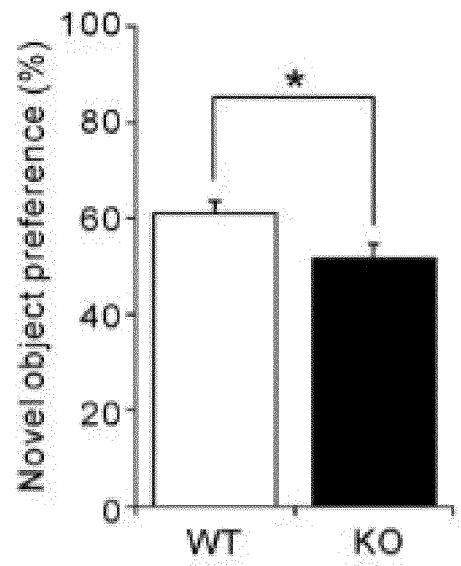
Figure 6C:
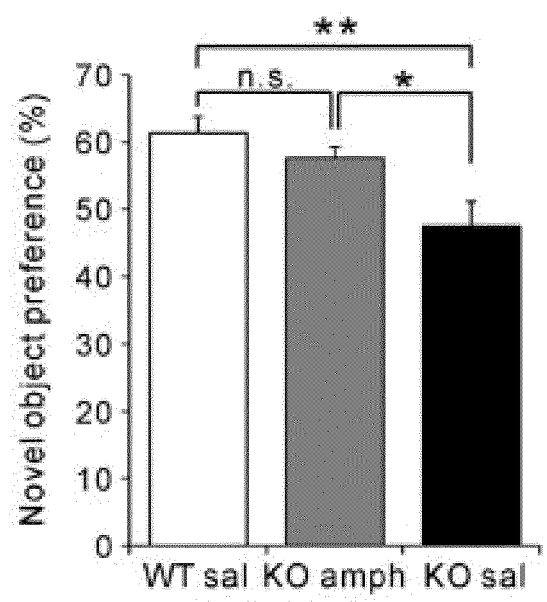

A novel object recognition test for assessment of object recognition and memory performance using the GIT1 knock-out mouse was performed in the same open space box as used in the open field test. The novel object recognition test included a sample phase and a test phase. During the sample phase, the mouse was allowed to detect the same two objects placed in an open space box for 10 minutes and, by video shooting the sample phase, times of observing both the objects by the mouse were recorded. As a result, it was found in FIG. 6A that a difference in object detection time between the normal mouse and the GIT1 knock-out mouse is not statistically significant. Further, one of the same two objects, for example, was replaced by a novel object not exposed to the mouse and, after 24 hours, a test period was proceeded. Such a test period was 10 minutes and a time of observing two objects by the mouse was measured during the test period. In this regard, if the nose end of the mouse contacts the object or the mouse heads for the object within 2 cm before the same, this was defined as the observation. For observing recovery of the object recognition and/or memory performance, the present inventive mouse was administered with amphetamine or saline through peritoneal injection at a dose of 4 mg/kg/day and placed in an open space box, 20 minutes before the sample phase. As a result of the present test, FIG. 6B demonstrated that the GIT1 knock-out mouse exhibited deteriorated novel object recognition ability, compared to the normal mouse. Moreover, it was confirmed from FIG. 6C that the object recognition ability can be recovered by an ADHD medicine, that is, amphetamine.

Example 6

Figure 7A:
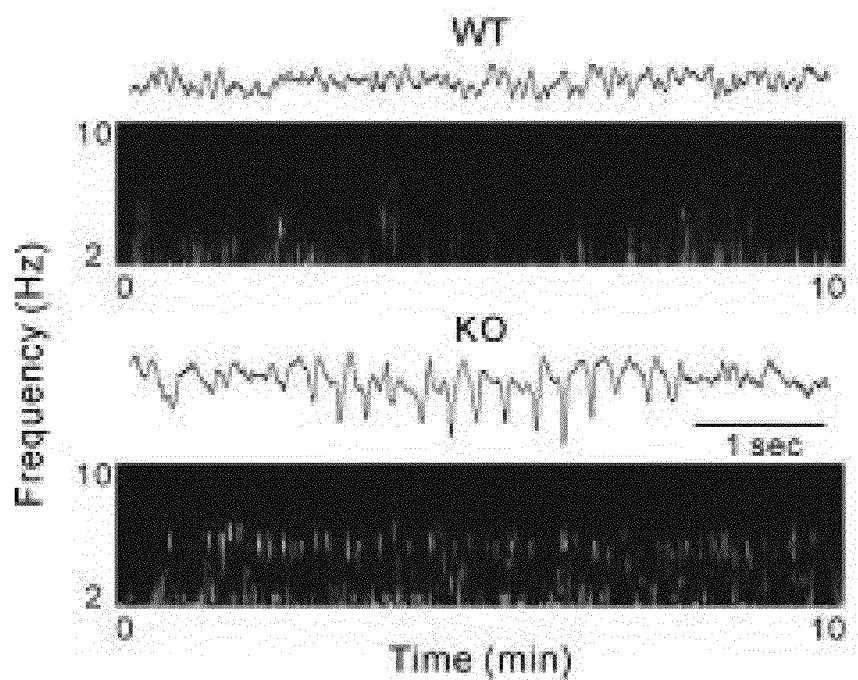
FIG. 7 illustrates an abnormal theta section waveform observed in the frontal lobe of GIT1 knock-out mice (FIG. 7A); a power spectrum density thereof (FIG. 7B); and recovery of the abnormal theta section waveform through amphetamine treatment (FIG. 7C)
Figure 7B:
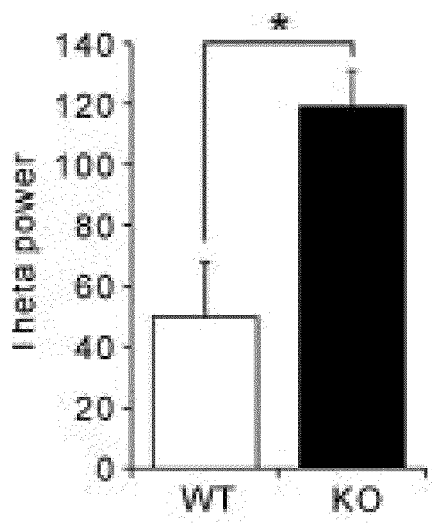
Figure 7C:
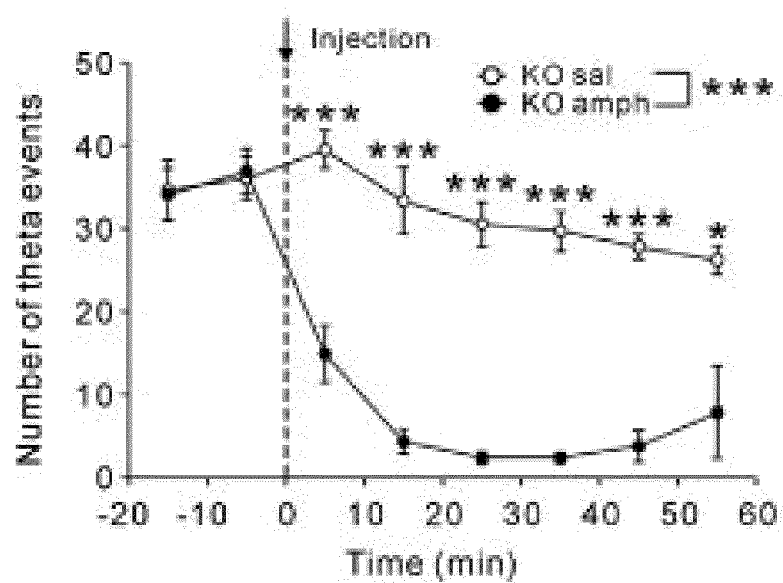
Figure 8:
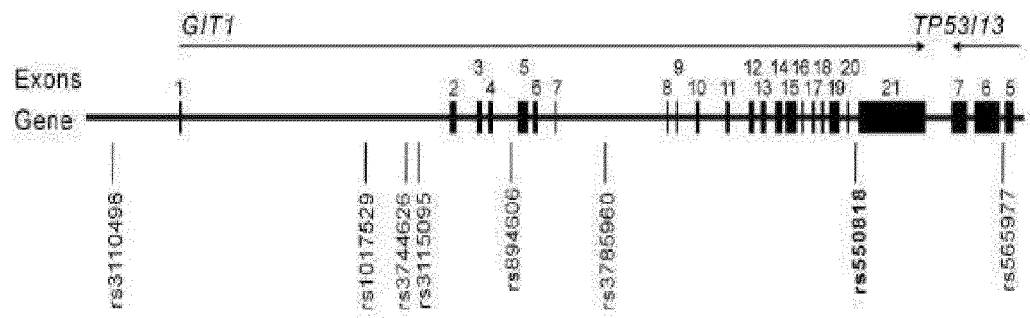
FIG. 8 shows single base multiplicity of one rs550818 present at 24926101 base site of chromosome 17 (Genome Build 36.3).

Analysis of Theta Section Waveform and Power Spectrum Density in GIT1 Knock-Out Mouse A process of assaying an abnormal theta section waveform and a power spectrum density in the frontal lobe using the GIT1 knock-out mouse according to the present invention was executed after administering ketamine to a mouse through peritoneal injection at a dose of 150 mg/kg to anesthetize the mouse and fixing the head of the mouse to a stereotaxic instrument. EEG electrodes were inserted into both the right frontal lobe and the left frontal lobe. More particularly, a correct fixing position was set by calculating a correct coordinate having the front side of 2.8 mm and each lateral side of 0.8 mm with reference to the bregma, via the stereotaxic instrument. A grounding electrode was inserted into the occipital lobe. After inserting the electrodes and 1 week recovery period, the mouse was placed in an EEG chamber to measure a brain wave for 1 hour. EEG signals were amplified using a Grass model 7H polygraph (Grass Technologies) and digitalized at a sampling frequency of 2000 Hz using DIGIDATA 1320A (Molecular Devices), followed by acquisition of data using pClamp8.0 program (Axon Instruments) and analysis thereof. Analyzed results are shown in FIG. 7 and, in particular, FIG. 7A illustrates an abnormal theta waveform shown in the frontal lobe of the GIT1 knock-out mouse; FIG. 7B shows a power spectrum density. Specifically, it can be seen from FIG. 7C that the abnormal theta waveform of the GIT1 knock-out mouse was favorably recovered, thus exhibiting recovery of hyperactivity and damaged memory of the mouse after administering amphetamine, compared to a control having saline administered thereto.

As set forth above, the present invention uses GIT1 knock-out mice to execute analysis of causes for attention deficit hyperactivity disorder, in particular, neuro-chemical factors, genetic factors and/or environmental factors, and finds causes for the foregoing diseases and other various anxiety disorders to provide the above mice as an animal model effective in screening a drug or medicine for protection or treatment of the diseases described above.

Accordingly, the spirit of the present invention is not particularly restricted to the exemplary embodiments described above and the scope of the present invention may include not only the subject matters defined by the appended claims but also modification and equivalents thereof.

What is claimed is:

1. A screening method of a drug for protection or treatment of attention deficit hyperactivity disorder (ADHD), comprising:
    (1) administering a candidate material of the drug for protection or treatment of attention deficit hyperactivity disorder (ADHD) to a homozygous GIT1 knock-out mouse;
    (2) after administration of the candidate material in operation (1), conducting an attention deficit hyperactivity disorder (ADHD) test of the mouse, wherein the ADHD test is at least one selected from Open field test, Home-cage activity test, Morris water maze test, Novel object recognition test, and Electroencephalogram; and
    (3) selecting the candidate material by which the attention deficit hyperactivity disorder (ADHD) is reduced as compared to a control group without administering the candidate material.

2. The method of claim 1, wherein the attention deficit hyperactivity disorder (ADHD) test in operation (2) is performed by using a homozygous GIT1 knock-out mouse having a disease characterized by at least one selected from attention deficit, hyperactivity, distrability and behavior disorders.

3. The method of claim 1, wherein the candidate material in operation (1) is a peptide, protein, non-peptide compound, synthetic compound, fermented product, cell extract, plant extract, animal tissue extract or plasma.

* * * * *